United States Patent [19]
Owens, Jr. et al.

[11] Patent Number: 5,897,840
[45] Date of Patent: Apr. 27, 1999

[54] MULTI-CHAMBERED URINE SPECIMEN CONTAINER FOR AUTOMATIC EXTRACTION AND HIGH FORENSIC INTEGRITY

[75] Inventors: Arthur Neal Owens, Jr.; Benjamin M. Bartilson, both of Hilliard; Eric G. Hassenpflug, Westerville; David A. Fingerhuth, Ostrander, all of Ohio; John F. Jemionek, Silver Springs, Md.; Thomas A. Pettenski, Columbus, Ohio

[73] Assignee: Battelle Memorial Institute, Columbus, Ohio

[21] Appl. No.: 08/895,502

[22] Filed: Jul. 16, 1997

[51] Int. Cl.[6] .................................. B01L 3/00
[52] U.S. Cl. .......................... 422/102; 422/99; 220/505; 220/506; 220/526; 600/573; 600/575; 600/580
[58] Field of Search ............................ 422/99, 100, 102; 600/573, 575, 577, 580; 220/505, 506, 526

[56] References Cited

U.S. PATENT DOCUMENTS

| | | |
|---|---|---|
| 3,629,873 | 12/1971 | Long .................................... 4/220 |
| 3,894,845 | 7/1975 | McDonald ......................... 422/102 X |
| 4,042,337 | 8/1977 | Griffith ................................ 422/102 |
| 4,064,760 | 12/1977 | Benjamin ........................... 73/863.52 |
| 4,109,530 | 8/1978 | Kim ...................................... 73/427 |
| 4,211,749 | 7/1980 | Kantner .............................. 422/102 |
| 4,244,920 | 1/1981 | Manschot et al. ................. 422/102 |
| 4,428,384 | 1/1984 | Raitto ................................. 600/573 |
| 4,473,530 | 9/1984 | Villa-Real .............................. 422/58 |
| 4,494,581 | 1/1985 | Gordon ........................... 422/102 X |
| 4,652,429 | 3/1987 | Konrad ............................... 422/102 |
| 4,852,560 | 8/1989 | Herman, Jr. et al. .............. 600/575 |
| 4,927,605 | 5/1990 | Dorn et al. ........................ 422/102 |
| 4,981,144 | 1/1991 | Carels, Jr. .......................... 600/573 |
| 5,380,289 | 1/1995 | Hemstreet et al. ................ 604/317 |
| 5,569,225 | 10/1996 | Fleury ................................ 604/323 |
| 5,599,331 | 2/1997 | Hemstreet et al. ................ 604/317 |
| 5,711,446 | 1/1998 | Jeffs et al. ..................... 220/506 X |

*Primary Examiner*—Maureen M. Wallenhorst
*Attorney, Agent, or Firm*—Standley & Gilcrest

[57] ABSTRACT

A urine specimen container is disclosed which includes multiple urine holding chambers and further includes a cap to be secured to the container that enables extraction of a portion of the urine specimen from one chamber within the container without contaminating the urine specimen contained in an adjacent chamber of the same container.

23 Claims, 3 Drawing Sheets

MULTI-CHAMBERED URINE SPECIMEN CONTAINER FOR AUTOMATIC EXTRACTION AND HIGH FORENSIC INTEGRITY

STATEMENT OF GOVERNMENT INTEREST

This invention was made with government support under Contract No. DAAD05-96-D-7019 awarded by the Department of Defense. The Government may have certain rights in this invention.

BACKGROUND AND SUMMARY OF THE INVENTION

The Present invention relates generally to container apparatus, and more particularly, to a multi-chambered urine specimen container with features including automated sample extraction and high forensic integrity.

Urine specimens are taken from people for a variety of reasons. Hospitals take a urine specimen from a patient to conduct laboratory test on the specimen to determine a patient's medical condition. Employers take urine specimens from employees to determine whether the employee has been using any illegal drugs. Recently, athletic competitions such as the Olympics have taken urine specimens from athletes to determine whether they have been using any illegal performance enhancing drugs. Such drug testing serves at least two purposes. First, it act as a deterrent by reminding those who would be tested that drug testing will be done and if they use an illegal substance they will in all likelihood be detected. The second function that drug testing serves is to identify drag users. For example, if an employee in a sensitive job is under the influence of narcotics, their job may be performed in a manner that is not safe and could result in harm to the employee as well as others.

The taking of a specimen from a person undergoing drug testing is usually done in the following manner. Usually, a person is selected to be tested, and asked to urinate into a specimen container while being observed by a witness. The donor places a lid on the specimen container and is then asked to put a label on the specimen container and to write the donor's social security number or other identifying number on the label thus providing the critical link between the donor's identity and the donor's specimen in the specimen container. The donor then delivers the now closed container to an administrator conducting the drug testing. Once the desired number of donors have supplied a specimen, the drug testing administrator delivers the specimens to a testing laboratory to undergo analysis for illegal substances. At the laboratory the urine within the container must be extracted from the container and placed into a test tube in order to be tested. Currently, this is accomplished through manual pouring. This can result in spillage and/or contamination of the specimen. It also requires extra time in the laboratory for such handling of the urine specimen.

In addition to the requirement for manual pouring, specimen containers suffer from other disadvantages. When the container is opened at the laboratory all of the specimen is exposed to external contaminants. In other words, there is no portion of the specimen that is sealed from eternal contaminants while leaving another portion of the specimen available for testing. In known specimen containers, if any foreign substance comes into contact with the specimen within the container, the question of specimen contamination may be subject to litigation.

The present invention overcomes many of the above-described disadvantages of known specimen containers. The present invention is a specimen collection container which provides enhanced security for urine specimens once they are collected. The present invention allows for automated extraction of samples in conjunction with all extraction device and it conforms to government agency protocols for testing in a forensic environment. The present invention is designed for urine collection, transport, and automated sampling. It provides significant benefits in the area of drug testing. The present invention includes multi-chambers and taper resistant/evident features for providing high forensic integrity. The container of the present invention consists of a multi-chambered cup and a cap. The cup has a inner wall and an outer wall. When the cup is mated with the cap, which also has an inner and outer wall, at least two concentric chambers are formed. Variations on the design of the present invention will allow for more than two chambers.

Upon collection of a urine specimen from a donor, urine is donated to fill the cup of the present invention to a level slightly above the inner wall. The cap is then assembled to the cup to divide the specimen into multiple parts. The cap seals the specimen in the cup and seals the liquid in the inner chamber from the liquid in the outer chamber(s). The configuration of the container allows the use of radial seals which are highly reliable without difficult alignment of the mating parts. The design of the cap would displace liquid from the cup if it were over filled. This maintains an air space to allow for expansion of the liquid without damage to the container if the specimen were to freeze during transport. In addition, in a preferred embodiment, teeth on the cup and cap deform and lock as the cap is screwed on. The design of the teeth prevents removal of the cap without great force that would damage the container.

The cap is preferably designed for separate access to the two chambers. A butyl rubber septum is preferably included within the cap to allow sampling from the inner chamber with a hypodermic needle. A foil or tin plastic film on top of the septum may be provided to show evidence of piercing or tampering with the specimen. Sampling through the septum is possible with automatic instruments. An alternate approach does not require the septum or foil. With this approach, automatic sampling can be done directly through the plastic cap.

Additional testing samples may be taken manually from the outer chamber of the cup through a pouring spout in another preferred embodiment of the present invention. Due to the seal between the two chambers, any possible contamination of the specimen in the inner chamber which occurred during automatic extraction would not have disturbed the specimen in the outer chamber(s). To sample from the outer chamber, the top of the pour spout is removed and the specimen is poured from the cup. A small cap may be placed over the pour spout to reseal the outer chamber(s).

The container is preferably injection molded from polyolefin. Butyl rubber may be used for the septum. These materials absorb littler or no drugs from the specimen and release no contaminants, thereby allowing accurate test results. The container is preferably designed with inexpensive materials, few parts, and relatively simple features in order to be cost effective.

DETAILED DESCRIPTION OF PREFERRED EMBODIMENT(S)

Figure 1:
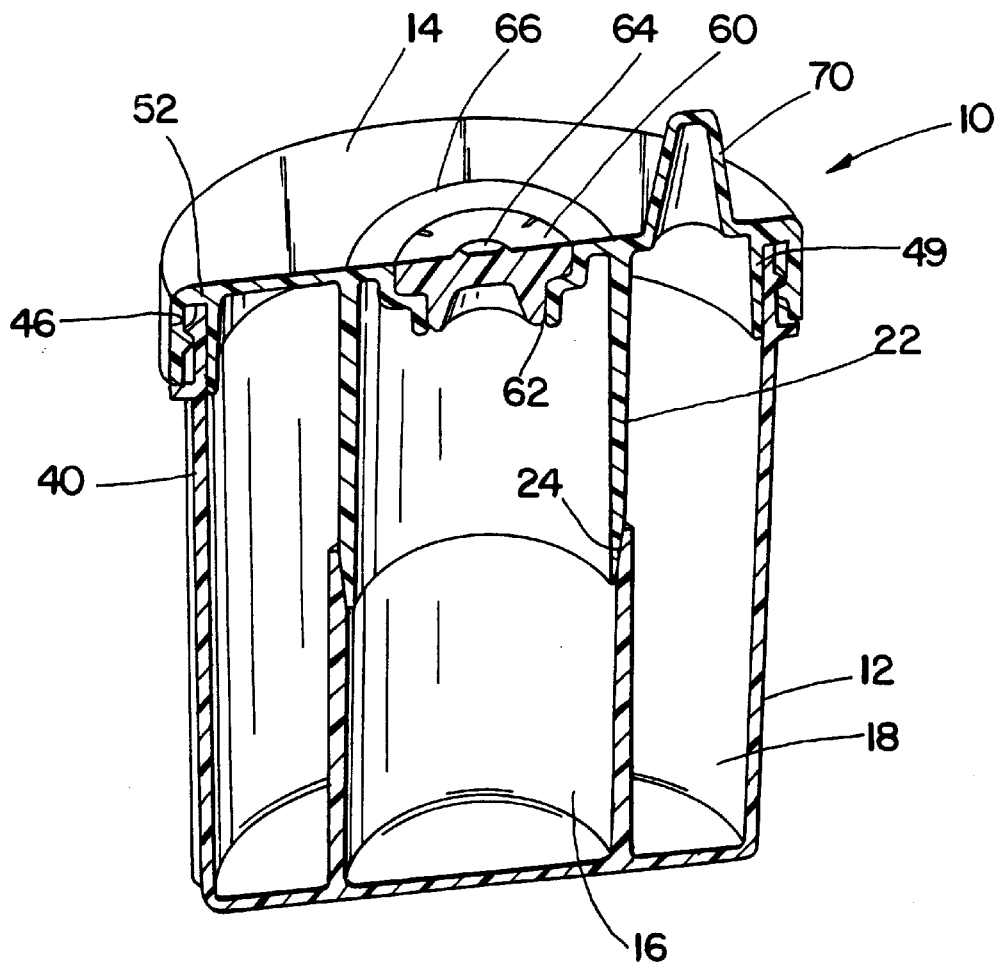
FIG. 1 shows a cross-sectional view of a preferred embodiment of the urine specimen container of the present invention.

Referring now to FIG. 1, there is shown generally at 10 a preferred embodiment of the present invention. In its most basic form the urine specimen container of the present invention includes a cup 12 and a cap 14. Within the cup 12 there are at least two chambers. An inner chamber 16 may be concentrically located within an outer chamber 18. A donor urinating into the open cup 12 would deposit urine in both the inner chamber 16 and the outer chamber 18 as a result of the inner chamber 16 preferably having a wall depth less than the depth of the outer chamber 18 wall.

Figure 5:
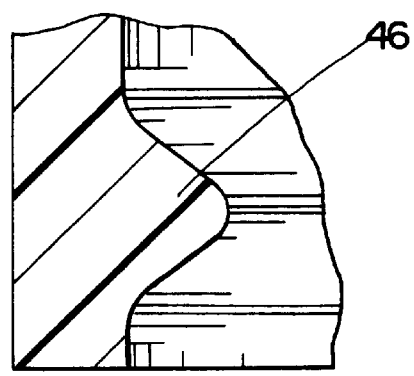
FIG. 5 shows a detail of another surface of the cap of FIG. 2.
Figure 9:
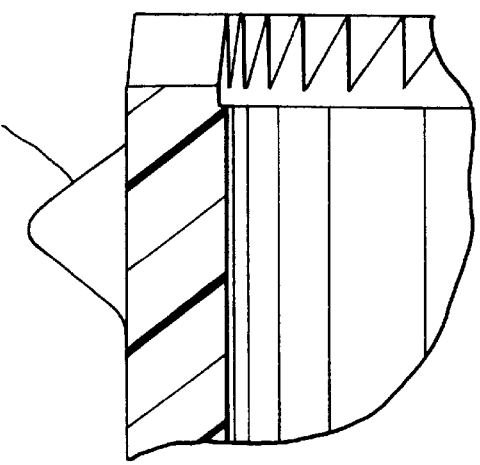
FIG. 9 is a detail view of another engagement surface of the cup shown in FIG. 6.

Once the urine is collected in the cup 12 the cap 14 is preferably threadably secured to the cup 12. In FIG. 9 a thread 44 is shown as it is formed as a part of wall 40 of the cup 12. The thread 44 is designed to ultimately ride against the thread 46 shown in FIG. 5 of the cap 14, holding the cap securely to the cup. Several unique features of the present invention act upon securement of the cap to the cup.

Figure 2:
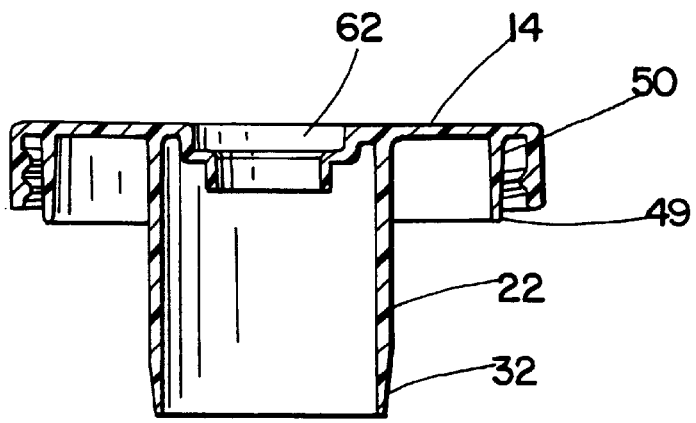
FIG. 2 shows a cross sectional view of the cap of the container of FIG. 1.
Figure 3:
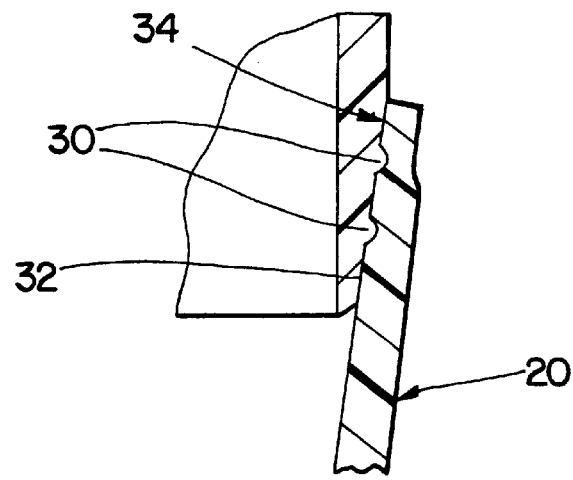
FIG. 3 shows a detail view of an engagement surface of the cap of FIG. 2.
Figure 6:
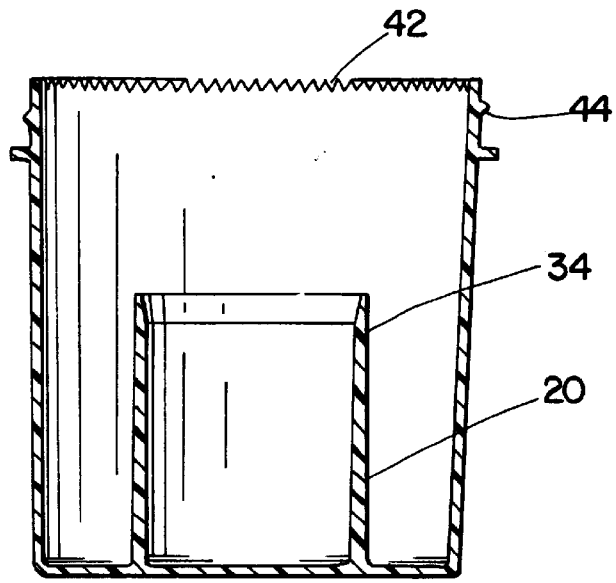
FIG. 6 shows a cross sectional view of the cup of the container shown in FIG. 1.
Figure 7:
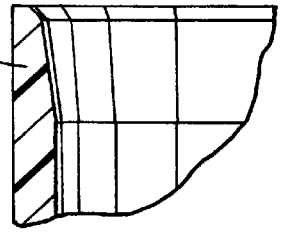
FIG. 7 shows a detail view of an engagement surface of the cup shown in FIG. 6.

The wall 20 of the inner chamber 16 contacts the mating wall 22 of the cap 14 at engagement surface 24. This is best shown in the details of FIG. 3 taken from the cross section view of the cap shown in FIG. 2, and FIG. 7 taken from the cross section view of the cup in FIG. 6. Ribs 30 are preferably provided on a tapered surface 32 as shown in FIG. 3 describing the mating wall 22 of the cap 14. The ribs 30 engage the tapered surface 34 shown in FIG. 7. When the cap 14 is threaded onto the cup 12, the ribs 30 are compressed against the surface 34. In is manner of securement the inner chamber 16 is sealed from the outer chamber 18 such that there is no fluid communication between the inner chamber 16 and the outer chamber 18 once the cap 14 is properly secured to the cup 12.

Figure 4:
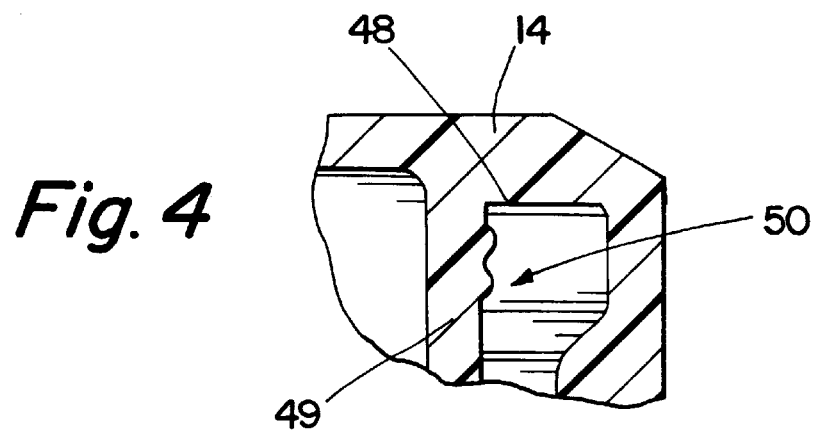
FIG. 4 shows a detail view of a second engagement surface of the cap of FIG. 2.

At the upper portion of the wall 40 of outer chamber 18, the cap 14 preferably engages the cup as follows. Ribs 50 are provided on the outer surface of a wall 49 which protrudes from the cap 14, as shown in FIG. 4. The ribs 50 engage the inner surface of the cup wall 40. When the cap 14 is threaded onto the cup 12, the ribs 50 are compressed against the inner surface of wall 40. In this manner of securement the outer chamber 18 is sealed from the outside environment.

Figure 8:
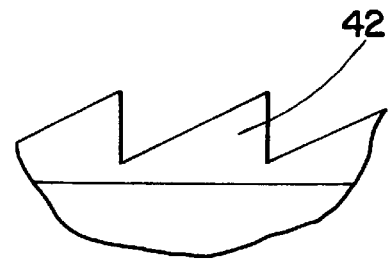
FIG. 8 is a detail view of a portion of the cup shown in FIG. 6.

In FIG. 8 there are shown locking teeth 42 on the cup 12. Similar teeth 48 on the cap 14 are located as shown in FIG. 4. As the cap 14 is threaded onto the cup 12 using the threads 44 and 46, the locking teeth 42 and 48 engage. The further the cap is screwed onto the cup, the greater the engagement of the teeth. The greater the engagement, the greater the resistance to unscrewing the cap. When the cap is screwed onto the cup the proper distance, the cap can not be removed without excessive force which would damage the cap and the cup. If the cap 14 were removed from the cup 12 prior to the container arriving at the testing laboratory, the removal of the cap 14 would be readily apparent from the structural damage caused by the breaking of the teeth engagements.

When the cap 14 is engaged to the cup 12, the walls 49 and 22 in the cap 14 create a trapped air zone above the urine within the container below the surface of the cap 14. This trapped air is useful if the volume of the urine is near the top of the cup and later freezes. Since the urine will expand during the transition from a liquid to a solid (freezing), the air space within the container will allow for expansion of the urine that would occur without damage to the container.

Referring again to FIG. 1, the cap 14 preferably includes a septum arranged within the cap to reside above the inner chamber 16 when the cap is secured to the cup. The septum 60 may be made of butyl rubber and may be press fit into a recess 62 formed within the cap 14. A target zone 64 within the center of the septum 60 is preferably adapted to receive an extraction tool such as a hypodermic needle. To further protect the container 10 from tampering, a foil seal 66 may be secured over the septum 60 using an adhesive, heat seal or other techniques. In this manner, it would be readily apparent if the foil seal 66 had been pierced or peeled away prior to arrival at the testing laboratory indicating the possibility of tampering or penetration of the septum.

An integral pour spout 70 may be formed within the cap 14 to provide a relatively easy way of accessing the outer chamber(s) 13 contents. For example, if testing had occurred from the inner chamber 16 via extraction through the septum 60, and such testing were to indicate that an illegal drug was detected, the specimen contained in the outer chamber 18 would remain sealed for later duplication and verification of the prior test on the contents of the inner chamber 16. Access to the urine contained in the outer chamber 18 may be obtained through the pour spout 70. The pour spout may be configured in a manner to simply be cut off by a pair of scissors or may be accessed with a hypodermic needle or any of several other means of withdrawal of the urine from chamber 18. An optional pour spout cap (not shown) may be tethered to the cap 14 to place over the then opened pour spout 70 to keep the contents of chamber 18 from spilling after opening.

In another embodiment of the present invention three or more interior chambers may be provided within the container. The three or more chambers may be arranged concentrically with each chamber having its own closure seal and withdrawal system. In another arrangement the three or more chambers may be disposed adjacent each other all within an outer chamber. While the preferred embodiment provides one cap with sealing means for all chambers, in another embodiment of the present invention, multiple caps may be provided to seal the respective chambers.

While in the preferred embodiment the contacting walls of the cap provide a seal with the walls of the chambers, in another embodiment of the present invention the walls of the cap may be threadably engaged with the walls of the chambers to provide the needed locking between the cap and the container. Other closure seal means may be provided in place of a wall seal. For example, a snap fit cap may be provided that includes a rib or similar member to be pressed into a relief formed in the walls of the chambers. In this manner, the chambers may be other than cylindrical in shape and would not necessarily have to be symmetrical chambers.

It should be recognized that many variations of the present invention fall within the scope of the following claims. The present invention may comprise more than two chambers and such chambers may be formed in different configurations than shown in the present drawings. The present invention may be manufactured in a number of different ways, but preferably the cap 12 and the cap 14 5 injection molded articles.

What is claimed is:

1. A urine specimen container, comprising:
   a cup including an inner chamber for receiving a first portion of a urine specimen and an outer chamber for receiving a second portion of said urine specimen, said inner chamber positioned inside said outer chamber; and
   a cap adapted to be secured to said cup thereby sealing said urine specimen from external contamination, said cap, while secured to said cup, adapted to enable extraction of said first portion of said urine specimen from said inner chamber and further adapted to enable extraction of said second portion of said urine specimen from said outer chamber, said cap adapted to enable extraction of one of said portions of said urine specimen independently of the other one of said portions of said urine specimen.

2. The urine specimen container of claim 1, wherein said cup and said cap are made of plastic, injection molded material.

3. The urine specimen container of claim 1, further comprising:
   a septum secured within said cap.

4. The urine specimen container of claim 3, further comprising
   a material seal secured to said cap over said septum.

5. The urine specimen container of claim 1, wherein said cap includes a wall member depending therefrom adapted to be engaged with a wall forming said inner chamber of said cup.

6. The urine specimen container of claim 1, wherein said cap includes a recess adapted to receive a wall of said outer chamber of said cup when said cap is secured to said cup, and wherein locking teeth are formed within a wall of said recess and engage said wall of said outer chamber.

7. The urine specimen container of claim 1, wherein said cap further includes an integral pour spout for fluid communication with said outer chamber.

8. The urine specimen container of claim 1, further comprising a second inner chamber adjacent said inner chamber, said second inner chamber positioned inside said outer chamber.

9. The urine specimen container of claim 1, further comprising a second inner chamber concentric with said inner chamber, said second inner chamber positioned inside said inner chamber.

10. The urine specimen container of claim 1, whereby said cap is threadably secured to said cup.

11. The urine specimen container of claim 1, whereby said cap is press fit to said cup.

12. The urine specimen container of claim 1, wherein said inner chamber is symmetrically centered within said cup.

13. A container for testing a fluid, said container comprising:
    a cup including at least one inner chamber for receiving a portion of said fluid and at least one outer chamber for receiving another portion of said fluid, said at least one inner chamber positioned inside said at least one outer chamber; and
    a cap adapted to be secured to said cup thereby sealing said fluid in said cup, said cap having at least one wall depending therefrom, said at least one wall having a tapered portion and at least one rib on the tapered portion adapted to depress said at least one inner chamber when said cap is secured to said cup such that said at least one wall prevents fluid communication between said at least one inner chamber and said at least one outer chamber when said cap seals said fluid in said cup.

14. The container of claim 13, wherein said fluid is urine.

15. The container of claim 13, wherein said cap further includes an extraction port in communication with said at least one inner chamber.

16. The container of claim 15, wherein said cap further includes a second extraction port in communication with said at least one outer chamber.

17. The container of claim 13, further comprising at least one raised rib on at least one engagement surface between said cap and said cup.

18. A urine specimen container, comprising:
    a cup including an inner chamber for receiving a first portion of a urine specimen and an outer chamber for receiving a second portion of said urine specimen, said inner chamber positioned inside said outer chamber;
    a cap adapted to be secured to said cup thereby sealing said urine specimen from external contamination, said cap including a septum for extraction of said first portion of said urine specimen from said inner chamber and further including an integral spout to enable extraction of said second portion of said urine specimen from said outer chamber, said cap adapted to enable extraction of one of said portions of said urine specimen independently of the other one of said portions of said urine specimen; and
    wherein an engagement surface between said cap and said cup includes at least one raised rib.

19. A urine specimen container, comprising:
    a cup including an inner cylindrical chamber for receiving a first portion of a urine specimen and an annular outer chamber for receiving a second portion of said urine specimen;
    a cap having a cylindrical wall depending therefrom for mating with said inner cylindrical chamber and secured to said cup thereby sealing said urine specimen from external contamination, said cap including a septum for extraction of said first portion of said urine specimen from said inner chamber and further including an integral spout to enable extraction of said second portion of said urine specimen from said outer chamber, said cap adapted to enable extraction of one of said portions of said urine specimen independently of the other one of said portions of said urine specimen; and
    wherein an engagement surface between said cap and said cup includes at least one raised rib.

20. A urine specimen container, comprising:
    a cup including an inner chamber for receiving a first portion of a urine specimen and an outer chamber for receiving a second portion of said urine specimen, said inner chamber positioned inside said outer chamber, a top portion of a wall of said inner chamber being lower than a top portion of a wall of said outer chamber; and a cap adapted to be secured to said cup thereby sealing said urine specimen from external contamination, said cap adapted to enable extraction of said first portion of said urine specimen from said inner chamber and further adapted to enable extraction of said second portion of said urine specimen from said outer chamber.

21. A urine specimen container, comprising:

a cup including an inner chamber for receiving a first portion of a urine specimen and an outer chamber for receiving a second portion of said urine specimen, said inner chamber positioned inside said outer chamber; and a cap adapted to be secured to said cup thereby sealing said urine specimen from external contamination, said cap adapted to enable extraction of said first portion of said urine specimen from said inner chamber and further adapted to enable extraction of said second portion of said urine specimen from said outer chamber, said cap having a wall member depending therefrom adapted to be engaged with a wall forming said inner chamber of said cup, said wall member of said cap including a tapered portion having at least one raised rib thereon.

22. A container comprising:

a cup having a first wall and a second wall, said first wall connected to said second wall to define a first chamber and a second chamber, said first chamber adapted to receive a first portion of a fluid, said second chamber adapted to receive a second portion of said fluid; and a cap adapted to be secured to said cup thereby sealing said fluid from external contamination, said cap, while secured to said cup, adapted to enable extraction of said first portion of said fluid from said first chamber and further adapted to enable extraction of said second portion of said fluid from said second chamber, said cap adapted to enable extraction of one of said portions of said fluid independently of the other one of said portions of said fluid.

23. The container of claim 22, wherein said cap is adapted to prevent fluid communication between said first chamber and said second chamber when said cap seals said fluid in said cup.

* * * * *

UNITED STATES PATENT AND TRADEMARK OFFICE
CERTIFICATE OF CORRECTION

PATENT NO. : 5,897,840
DATED : Apr. 27, 1999
INVENTOR(S) : Arthur Neal Owens, Jr., et al It is certified that error appears in the above-indentified patent and that said Letters Patent is hereby corrected as shown below:

In Column 1, line 21, please delete the word "test" and replace it with the word -- testing --

In Column 1, line 32, please delete the word "drag" and replace it with the word -- drug --

In Column 2, line 4, please delete the word "all" and replace it with the word -- an --

In Column 2, line 12, please delete the word "a" and replace it with the word -- an --

In Column 3, line 45, please delete the word "is" and replace it with the word -- this --

In Column 4, line 29, please delete the number "13" and replace it with the number -- 18 --

Signed and Sealed this

Second Day of November, 1999

Attest:

Attesting Officer

Q. TODD DICKINSON

Acting Commissioner of Patents and Trademarks